United States Patent [19]
DeCote, Jr.

[11] Patent Number: 4,677,986
[45] Date of Patent: Jul. 7, 1987

[54] UNSATURABLE SENSE AMPLIFIER FOR PACER SYSTEM ANALYZER

[75] Inventor: Robert DeCote, Jr., Miami Beach, Fla.

[73] Assignee: Cordis Corporation, Miami, Fla.

[21] Appl. No.: 738,608

[22] Filed: May 28, 1985

[51] Int. Cl.⁴ .............................................. A61B 5/04
[52] U.S. Cl. .............................. 128/697; 128/419 PT; 128/901; 128/902
[58] Field of Search ............. 128/419 P, 419 PG, 696, 128/597, 901, 902, 908

[56] References Cited

U.S. PATENT DOCUMENTS

| | | | |
|---|---|---|---|
| 3,587,562 | 6/1971 | Williams | 128/908 |
| 3,757,790 | 9/1973 | Herrmann. | |
| 3,777,762 | 12/1973 | Nielsen. | |
| 3,783,877 | 1/1974 | Bowers | 128/419 PS |
| 3,800,801 | 4/1974 | Gaillard. | |
| 3,920,024 | 11/1975 | Bowers | 128/419 P |
| 4,245,643 | 1/1981 | Benzing, III et al. | |
| 4,290,430 | 9/1981 | Bihn et al. | |
| 4,325,384 | 4/1982 | Blaser et al. | 128/902 |
| 4,337,776 | 7/1982 | Daly et al. | |
| 4,436,093 | 3/1984 | Belt | 128/419 PG |

OTHER PUBLICATIONS

A New Electronic System for the Detection of Stimulated Cardiac Response, J. Mugica, B. Lazarus, D. Delle-Vedove, Y. Lallemand, O. Hubert.

Primary Examiner—William E. Kamm
Attorney, Agent, or Firm—Lockwood, Alex, FitzGibbon & Cummings

[57] ABSTRACT

An unsaturable cardiac sense amplifier includes first and second amplifying stages, each of which is subject to saturation by excessive input voltage. Input voltage to the first amplifier stage is limited to less than a saturating level by means of a pair of parallel, oppositely sensed, diodes. Saturation of the second amplifier stage is prevented by a degenerative feedback loop formed by a pair of serially connected zener diodes. An artifact squelch circuit, connected to the output of the second amplifier stage, limits the maximum output voltage of the sense amplifier.

10 Claims, 4 Drawing Figures

UNSATURABLE SENSE AMPLIFIER FOR PACER SYSTEM ANALYZER

BACKGROUND OF THE INVENTION

The present invention relates generally to a method and apparatus for monitoring a patient's heart, and more particularly to a sense amplifier for sensing and amplifying intracardiac impulses produced during contractions of the heart. The sense amplifier is particularly well adapted for use in a pacer system analyzer, wherein the operation of a pacer is monitored in association with a patient's heart prior to implantation.

To assist physicians in treating cardiac disorders of the type for which the use of implantable cardiac pacers is indicated, pacer system analyzers (PSA's) have been developed. These devices are used at the time of pacer implantation to efficiently measure the parameters of a pacer system, including a patient's heart, a pacer and implanted pacer leads, without the need to perform separate procedures requiring multiple interconnections and an undesirably long time period to complete. Pacers to be implanted are tested for proper programming and operation, not only while connected in a simulated pacing system environment, but also while operating in the actual system in which they are to be used. Moreover, pacer system analyzers are preferably equipped to generate pacing pulses as required to support the patient during the pacer implantation process, independently of the pacer to be implanted.

By using a pacer system analyzer, a physician is able to adjust the operating parameters of a pacer system as required to suit the specific needs of an individual patient before the pacer has been fully implanted and the implantation surgery completed. This minimizes the need for inconvenient and potentially injurious post-implantation adjustment of the pacer or its associated pacer leads.

In measuring several of the pacer system operating parameters, it is often necessary to sense and amplify the intracardial electrical signals which are produced in response to both naturally occurring, and artificially induced cardiac events. The sensing and amplification of these typically low-level cardiac signals is complicated not only by the presence of the periodically applied pacing pulses, but also by randomly occurring extraneous noise impulses or motion artifacts, which may exceed the intracardiac signal level by several orders of magnitude. Sense amplifier saturation, resulting from the occurrence of high level pacing pulses and artifacts, is undesirable since total amplifier insensitivity results during the period of saturation. Following saturation, amplifier gain will be reduced and will slowly increase to the normal value in a non-linear fashion as the amplifier recovers. Disruption of quiescent operating bias voltage points caused by amplifier saturation generally increases battery current drain, while increased stress on circuit components reduces reliability of the system. It is therefore desirable that sense amplifier saturation be avoided.

Prior sense amplifiers have avoided saturation by providing suitable blanking circuitry in the input or output circuits of the amplifier. The blanking circuits typically included analog switch devices which were actuated by means of a digital control signal applied during generation of each cardiac pacing pulse. Since these systems relied on the generation of appropriately timed logic control voltages, saturation could still result from random noise or from artifacts occurring between generated pacing pulses.

The present invention is directed to an unsaturable sense amplifier. To this end, the input and output circuits of the amplifier are each provided with blanking circuits which are actuated in response to input or output signals exceeding predetermined fixed limits rather than by the application of logic control voltages as in prior circuits. Accordingly, the sense amplifier as described herein will be automatically blanked by potentially saturating signals regardless of when they occur or where they originate. Thus, an essentially unsaturable sense amplifier is provided.

In view of the foregoing, it is a general object of the present invention to provide a new and improved sense amplifier for sensing intracardiac electrical signals indicative of a patient's cardiac activity.

It is a more specific object of the present invention to provide an improved sense amplifier which is not saturated by the presence of applied high level pacing pulses.

It is a still more specific object of the present invention to provide an improved sense amplifier which is not saturated by the occurrence of random noise or motion artifacts.

SUMMARY OF THE INVENTION

An unsaturable sense amplifier for use within a pacer system analyzer is provided and serves to sense and amplify intracardiac signals induced in response to applied pacing pulses. The amplifier includes a first amplifier stage which is subject to saturation by voltage on its input exceeding a first saturation level. A second amplifier stage, coupled to the output of the first amplifier stage, is subject to saturation by voltage at its input exceeding a second saturating level. An input limiter is provided for limiting the voltage on the input of the first amplifier to less than the first saturating level. An output limiter, connected between the input and output of the second amplifier stage, prevents the voltage at the input of the second amplifier from exceeding the second saturating level. An artifact squelch circuit coupled to the output of the second amplifier stage automatically squelches the output thereof when the voltage appearing thereon exceeds a predetermined squelch level.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
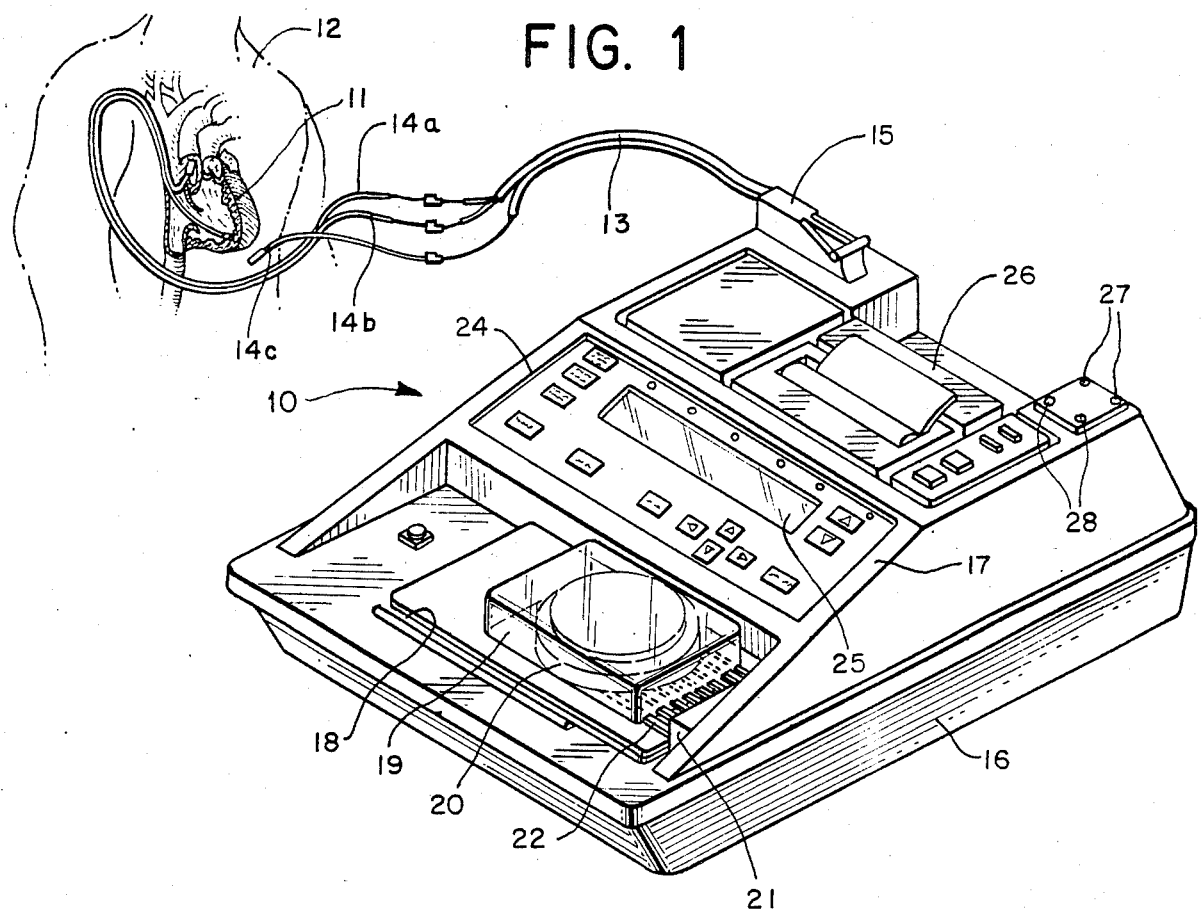
FIG. 1 is a perspective view of a pacer system analyzer incorporating a dual channel sense amplifier constructed in accordance with the invention.

Referring to the figures, and particularly to FIG. 1, a pacer system analyzer (PSA) 10 is shown which incorporates a dual-channel unsaturable sense amplifer constructed in accordance with the invention. As illustrated, the analyzer 10 is connected to the heart 11 of a patient 12 by means of a patient cable assembly 13 having a plurality of clip leads at one end which connect to the exposed ends of atrial and ventricular pacing leads 14a, 14b, and 14c of known construction. At its other end, the cable assembly is electrically connected to the analyzer by means of a multicontact connector 15.

Pacer system analyzer 10 is contained within a generally rectangular housing 16 formed of a durable, insulating plastic or like material and includes a sloping, generally flat, control panel 17. A portion of the housing is formed to provide a receptacle 18 for receiving a sealed package 19 containing a sterile implantable cardiac pacer 20. A connector 21 in recess 18 engages a plurality of electrical contacts 22 formed on package 19 to provide electrical communication between the analyzer 10 and pacer 20.

Panel 17 includes a plurality of pressure sensitive user-actuable push button controls on keyboard 24 and a liquid crystal display (LCD) 25. Pacer system analyzer 10 operates in one of several user-selected modes in accordance with entered key stroke commands. To assist the user in selecting the appropriate operating mode, a series of internally generated instructions and plurality of measured pacer system operating parameters are displayed on LCD 25. A plotter mechanism 26 provides EGM plots and a printed record of measured pacer system operating parameters and measured patient parameters, while two pairs of EGM electrodes 27 and 28 provide isolated atrial and ventricular cardiac signals for connection to external instrumentation.

The heart 11, patient cable assembly 13, patient lead set 14a–14c and pacer 20 together form a pacer system. Pacer system analyzer 10 functions to automatically measure various parameters of this system and to thereby assist a physician in selecting, implanting and adjusting the pacer system components for maximum effectiveness. Additionally, proper operation of the system can be verified before final implantation, and pacing pulses for supporting the patient during pacer system implantation can be generated.

Figure 2:
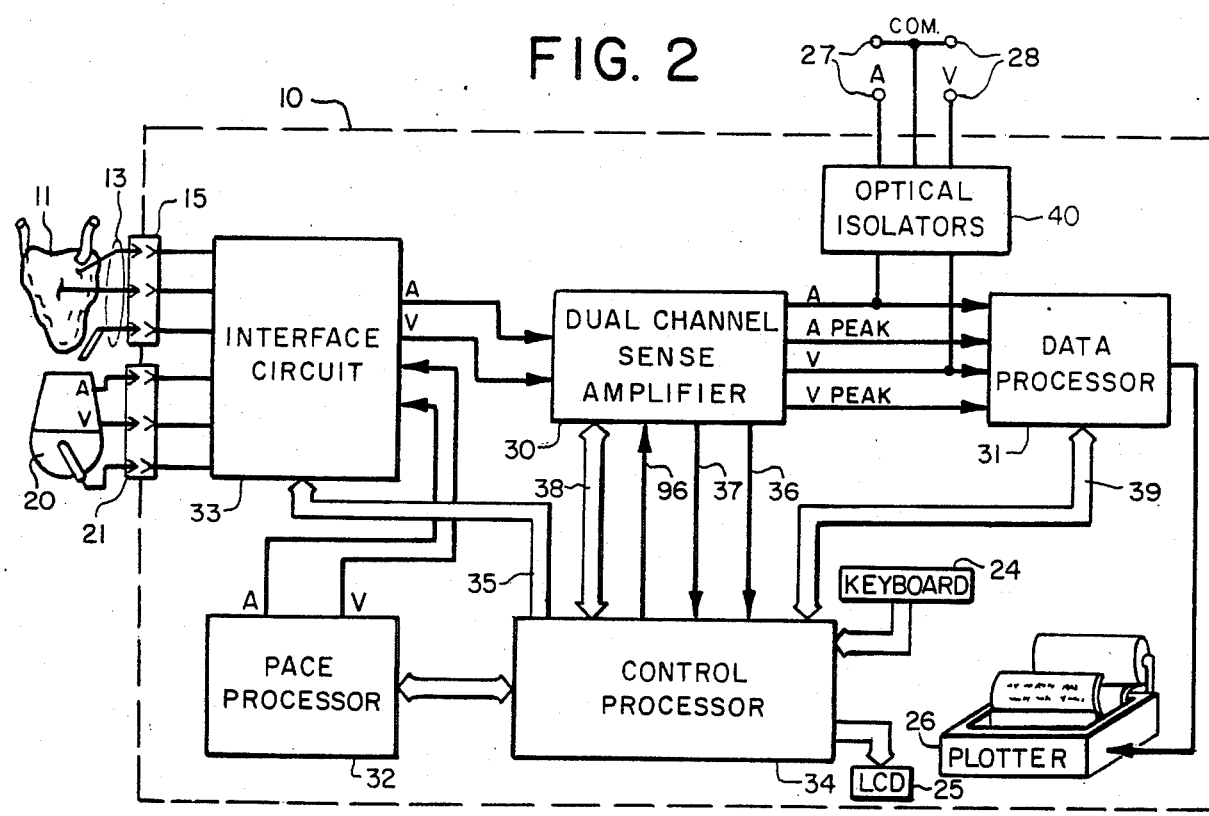
FIG. 2 is a simplified functional block diagram of the pacer system analyzer illustrated in FIG. 1 showing the principal subsystems thereof.

Referring to the simplified functional block diagram of FIG. 2, Pacer system analyzer 10 includes a dual channel sense amplifier 30 constructed in accordance with the invention for amplifying sensed cardiac signals, a data processor 31 for processing the sensed signals, a pace processor 32 for generating atrial and/or ventricular pacing signals, an interface circuit 33 for coupling the patient's heart 11 and implantable pacer 20 to the pacer system analyzer, and a control processor 34 for controlling the operation of the analyzer components. Control processor 34 is preferably microprocessor based and is programmed to generate system control voltages in response to user-entered keystroke commands from keyboard 24. Additionally, the control processor may generate a series of user instructions for display on LCD 25.

To facilitate measurement of patient parameters and to provide basic patient life support, pace processor 32 generates pacing pulses for application to heart 11. Atrial and ventricular pacing pulses of predetermined amplitude, duration and rate are generated in accordance with applied pace control signals from control processor 34. The pacing pulses are outputted from the pace processor through interface circuit 33 for application to the heart 11 through cable assembly 13.

As further illustrated in FIG. 2, pacer 20 is connected by connector 21 to interface circuit 33. Upon application of an appropriate control signal from control processor 34 through control bus 35, interface circuit 33 couples cable assembly 13 to pacer 20 whereupon the heart is paced by the pacer. Accordingly, the control processor can cause the heart to be paced by either PSA pace processor 32 or by implantable pacer 20.

Atrial and/or ventricular intracardiac signals detected by cable assembly 13 are applied to respective inputs of dual-channel sense amplifier 30. The sense amplifier generates atrial and/or ventricular strobe signals for application to control processor 34 through conductors 36 and 37 upon the occurrence of atrial or ventricular intracardiac signals above a predetermined sense threshold. The control processor sets the atrial and ventricular sense thresholds by applying digitally encoded instructions to the amplifier through a data bus 38. The sense amplifier further includes capture sensing circuitry for detecting cardiac contractions induced by applied pacing pulses. When capture is detected, a signal is applied to control processor 34 through data bus 38.

Additionally, the dual-channel sense amplifier provides amplified atrial and ventricular signals for application to data processor 31 and for application to EGM terminals 27 and 28 through an isolation circuit 40, as well as signals indicative of the peak atrial lead P and R waves and ventricular lead R-waves sensed. In response to instructions from control processor 34, via control bus 39, the data processor 31 performs the mathematical operations required to calculate various patient or pacer system operating parameters for display on LCD 25 or for printing by plotter 26.

Figure 3:
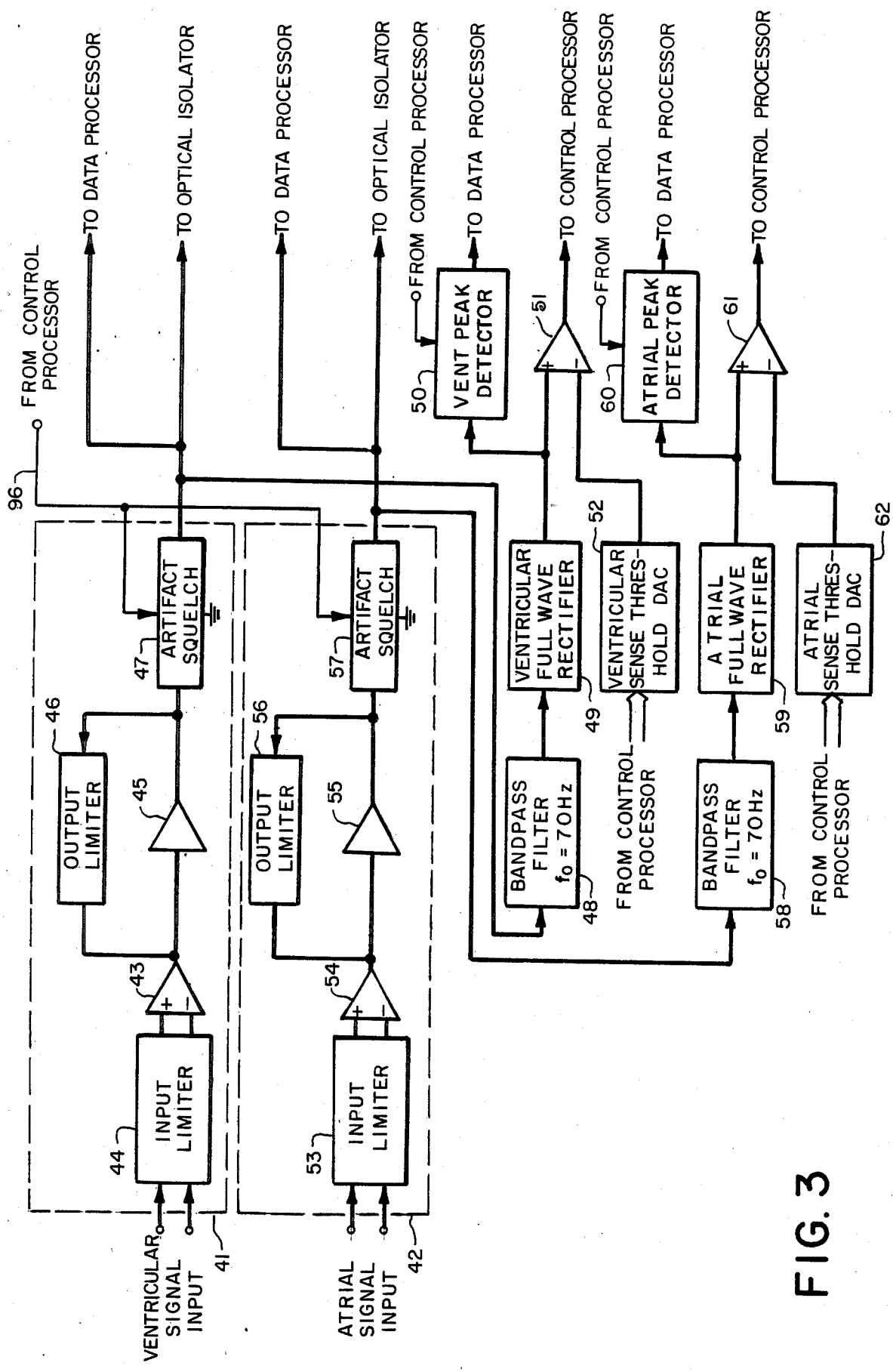
FIG. 3 is a simplified block diagram of the dual channel sense amplifier incorporated in the pacer system analyzer of FIG. 1.

Referring to FIG. 3, the dual channel sense amplifier 30 (FIG. 2) includes an unsaturable ventricular amplifier channel 41 and an unsaturable atrial amplifier channel 42. Ventricular intracardiac signals are coupled from interface circuit 33 (FIG. 2) to amplifier channel 41. Amplifier channel 41 includes a first amplifier stage 43 which differentially amplifies the applied cardiac signal while rejecting undesired common mode signal components. To avoid saturation of amplifier stage 43, channel 41 includes, in accordance with the invention, an input limiter stage 44 which permits signals below a threshold level to pass through unattenuated but which attenuates signals above this threshold.

The output of ampifier stage 43 is applied to the input of a second amplifier stage 45. To avoid saturation of amplifier stage 45, its output is, in accordance with the invention, coupled back to the input of the amplifier through output limiter stage 46 to form degenerative feedback loop. The output limiter stage 46 comprises a non-linear device which provides negligble degenerative feedback when the output of amplifier stage 45 is less than that which would result with saturation thereof, but which provides appreciable degenerative feedback when the output increases to a level approaching saturation. Preferably, output limiter stage 46 is constructed to provide whatever degree of feedback is required to avoid saturation of amplifier stage 45.

Motion artifacts are typically of a longer duration than artificial pacing pulses or randomly occurring noise impulses, and hence may not be fully blocked by the input and output limiters. Accordingly, amplifier channel 41, in accordance with another aspect of the invention, is provided with an artifact squelch circuit 47. This circuit, which is connected to the output of amplifier stage 45, presents a high impedance to ground for signals below a predetermined squelch level and a very low impedance for signals above the squelch level. Accordingly, the output of amplifier stage 41 is equal to the output of amplifier stage 45 for signal levels below the artifact squelch level, and is near-zero for signals above that level. In addition, squelching can be synchronized to pacer output pulses via a line 96 from control processor 34.

The output of the artifact squelch circuit 47 is connected to input ports of data processor 31 and optical isolator 40 (FIG. 2). To improve noise rejection in the sense amplifier channel, the output is also connected to a bandpass filter 48 having a center frequency of 70 Hz. A full wave rectifier 49, coupled to the output of bandpass filter 48, converts the filtered signal from amplifier 41 to a corresponding absolute value voltage.

A peak detector circuit 50, coupled to the output of rectifier 49, develops an analog voltage corresponding to the peak value of the ventricular intracardiac signal. This voltage is applied to the data processor to facilitate automatic measurement of various patient parameters. The peak detector is reset by the control processor.

The ventricular sense amplifier also generates a strobe signal upon the occurrence of ventricular intracardiac signals having signal strengths in excess of a predetermined variable threshold level. To this end, the sense amplifier includes an analog comparator 51 having its non-inverting input coupled to the output of ventricular full wave rectifier 49 and having its inverting input coupled to the output of a sense threshold digital-to-analog converter (DAC) 52. DAC 52 develops a reference voltage which is applied to comparator 51 to establish a sense threshold level which, when exceeded by the level of the rectified ventricular signal, causes the comparator to produce a logic level output. The magnitude of the sense threshold level is set by means of a digitally encoded instruction developed by the control processor and applied to DAC 52 through control bus 38 (FIG. 2).

The dual channel sense amplifier 30 includes an atrial amplifier channel for amplifying the intracardiac signals sensed by the atrial cardiac lead. The atrial channel, which may be identical to the ventricular signal channel heretofore described, includes an input limiter stage 53, a differential first amplifier stage 54, a second amplifier stage 55, an output limiter stage 56 and an artifact squelch circuit 57, which are connected for operation in the same manner as the corresponding elements in the ventricular signal channel. Similarly, a bandpass filter 58, an atrial full wave rectifier 59, an atrial signal peak detector circuit 60, a comparator amplifier 61 and an atrial sense threshold DAC 62 are connected for operation in the same manner as the corresponding elements in the ventricular signal channel. It will be appreciated, however, that the operational characteristics of each of the elements in the atrial signal circuit can be adjusted for optimum performance with actual atrial intracardiac signals, and accordingly need not be identical with the corresponding elements of the ventricular signal channel.

Figure 4:
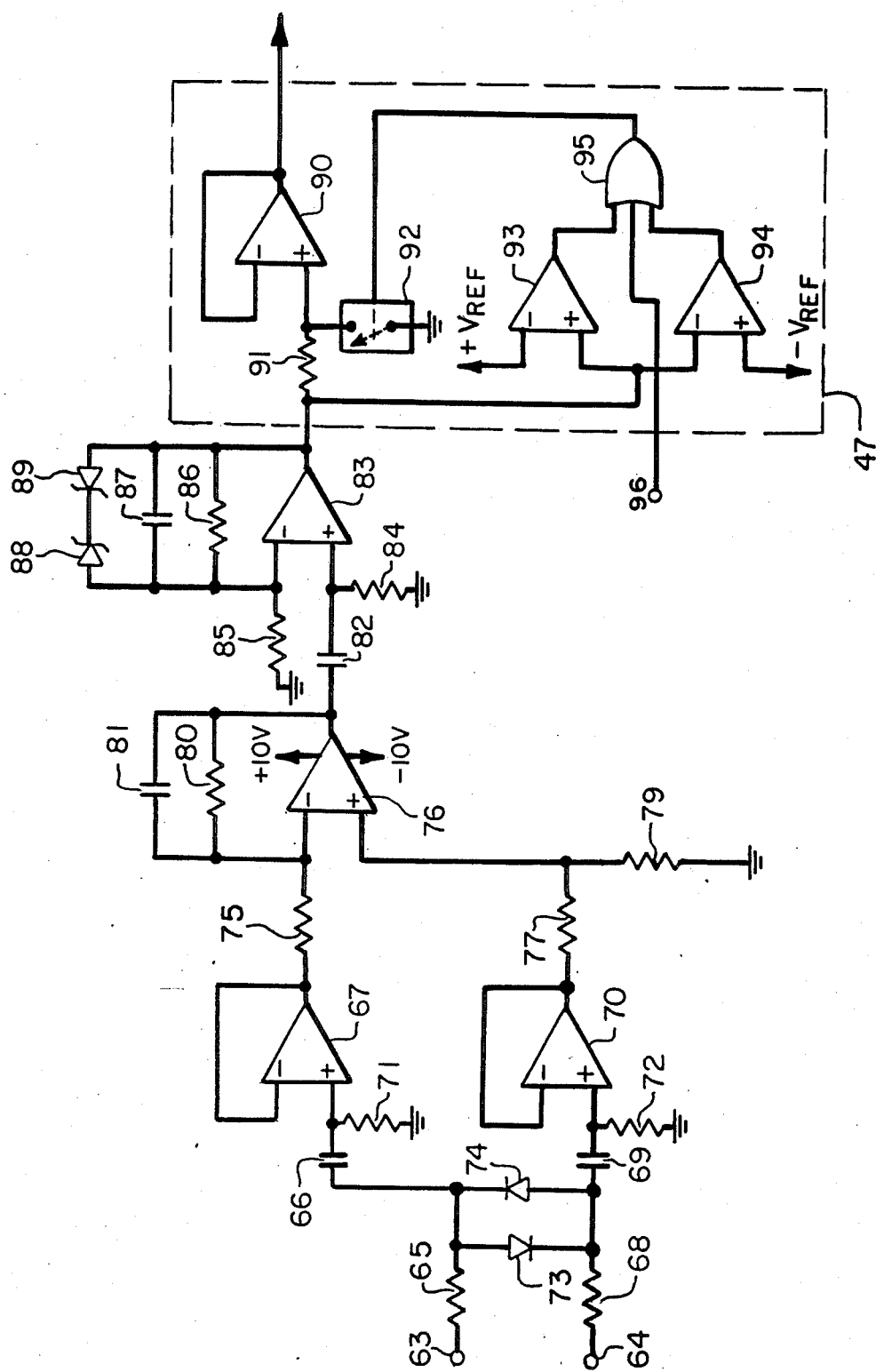
FIG. 4 is a schematic circuit diagram of one channel within the sense amplifier of FIG. 3.

A practical embodiment of the unsaturable amplifier channel 41 is shown in FIG. 4. Ventricular signals applied to ventricular sense amplifier input terminals 63 and 64 of the amplifier channel are coupled through a resistor 65 and a capacitor 66 to the input of voltage follower amplifier 67, and through a resistor 68 and capacitor 69 to the input of voltage follower amplifier 70. The inputs of the buffer amplifiers are connected to ground by resistors 71 and 72 respectively. Amplifiers 67 and 70 and their associated circuitry comprise the amplitude-limiting input stage of the amplifier channel.

To limit the maximum differential voltage between the inputs of amplifiers 67 and 70, an amplitude limiting circuit comprising a pair of Schottky diodes 73 and 74 is provided. The anode of diode 73 and cathode of diode 74 are connected to the juncture of resistor 65 and capacitor 66, and the cathode of diode 73 and anode of diode 74 are connected to the juncture of resistor 68 and capacitor 69. With this arrangement, the peak input signal level which can be applied to voltage-follower amplifiers 67 and 70 is limited to $\pm V_f$, where $V_f$ is the forward-bias voltage of diodes 73 and 74. Typically, the range of input intracardiac signals is well below $\pm V_f$.

The output of voltage-follower amplifier 67 is coupled through a resistor 75 to the inverting input of an amplifier 76, which comprises the differential first amplifier stage of the amplifier channel. The output of voltage-follower amplifier 70 is coupled through a resistor 77 to the non-inverting input of this amplifier. Degenerative feedback for amplifier 76 is provided by a resistor 80 and a parallel-connected capacitor 81 which causes the gain of amplifier 76 to roll-off as frequency increases.

The output of differential amplifier stage 76 is coupled through a capacitor 82 to the non-inverting input of an amplifier 83, which comprises the second amplifier stage of the channel. The non-inverting and inverting inputs of amplifier 83 are coupled to circuit ground through resistors 84 and 85, respectively. Degenerative feedback for amplifier 83 is provided by a resistor 86 and parallel-connected roll-off capacitor 87.

To prevent saturation of ampifier 83, output limiting means are provided in the form of a pair of series-connected, oppositely-sensed, zener diodes 88 and 89 connected between the amplifier output and the inverting input terminal of the amplifier. In the event the output amplitude exceeds the zener breakdown voltage of either diode 88 or 89, negative feedback will adjust itself as required to maintain the output of amplifier 83 at essentially the threshold voltage of the diodes plus the forward voltage drop of one diode. By connecting the zener diodes as shown, amplitude limiting feedback will be provided during both the positive and negative portions of output voltage excursions.

By way of example, in an actual circuit, Schottky diodes 73 and 74 may be selected to have $V_f = 350$ mV to provide a peak input threshold of $\pm 350$ millivolts, and amplifier 76 may have a voltage gain of approximately 20. With these values, the maximum (limited) output voltage of amplifier 76 is a nominal $\pm 7$ volts. Assuming a typical maximum input cardiac signal of $\pm 25$ mV, the linearly amplified cardiac signal out of amplifier 76 will not exceed $\pm 500$ mV.

By way of further example, amplifier 83 may have a voltage gain of 5, resulting in an overall nominal gain in the amplifier channel of 100. The linearly amplified cardiac signals from amplifier 76, which attain a maximum of $\pm 0.5$ volts, can easily be amplified by amplifier 83 to $\pm 2.5$ volts without saturation. However, with typical supply voltages of $\pm 10$ volts DC, maximum amplitude output signals (±7 volts) from amplifier 76 would result in saturation of amplifier 83. Accordingly, zener diodes 88 and 89 are selected so as to avoid saturation of amplifier 83 and by way of example may each have a zener breakdown voltage of 6.8 volts; well above the cardiac signal limit.

Referring further to FIG. 4, the artifact squelch circuit 47 is seen to include a voltage follower 90 having its input coupled through a resistor 91 from the output of amplifier 83. The artifact squelch circuit further includes analog switch 92 connected between the input of voltage follower 90 and circuit ground. In response to an applied high level logic control signal, switch 92 becomes conductive, thereby shunting the non-inverting input to ground and causing the output of amplifier 90 to become nearly zero.

The artifact squelch circuit operates by causing analog switch 92 to automatically become conductive whenever signal levels in excess of a potentially saturating level are applied to voltage follower 90. To this end, the circuit includes a pair of comparators 93 and 94 as well as an OR gate 95 as shown. The output of amplifier 83 is applied to the non-inverting input of comparator 93 and to the inverting input of comparator 94. A positive polarity reference voltage $+V_{ref}$ is applied to the non-inverting input of comparator 93 and a negative polarity reference voltage $-V_{ref}$ is applied to the non-inverting input of comparator 94. By way of example, $\pm V_{ref}$ may be ±3 volts. The outputs of comparators 93 and 94 are each connected to the inputs of OR gate 95, the output of which is connected to the control input of analog switch 92.

When connected in this manner, comparators 93 and 94, and OR gate 95, establish a voltage "window" within which the output of the gate is low, and within which analog switch 92 is open. If the output of amplifier 83 swings beyond $\pm V_{ref}$, the output of gate 95 will go logic high, causing switch 92 to become conductive. Accordingly, for below threshold input signals, the output of voltage follower 90 will correspond to the applied input signal, but will become zero in the event out-of-window voltages are detected at the output of amplifier 83.

The three input OR gate 95 also allows for microprocessor controlled squelch action via line 96. When this input is brought to logic high, the output of OR gate 95 goes high, closing analog switch 92, as before. Thus, the automatic squelch action can be augmented by microprocessor controlled squelch action, as desired.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. An unsaturable sense amplifier for use in a pacer system analyzer to sense and amplify intracardiac signals induced in response to pacing pulses being applied to the heart of a patient, comprising:

first amplifier means for amplifying an applied voltage and being subject to saturation by said applied voltage exceeding a first predetermined saturating level;

second amplifier means coupled to the output of said first amplifier means for amplifying said output of said first amplifier means and being subject to saturation by said output exceeding a second predetermined saturating level;

input limiting means coupled to the input of said first amplifier means for limiting said applied voltage to less than said first predetermined saturating level;

output limiting means connected between the input and output of said second amplifier means for limiting said input of said second amplifier means to less than said second predetermined saturating level; and artifact squelch means coupled to said output of said second amplifier means for squelching said output when said output exceeds a predetermined squelch level.

2. An unsaturable sense amplifier as defined in claim 1 wherein said first amplifier means comprises a differential amplifier responsive to the differential voltage applied between a pair of input terminals.

3. An unsaturable sense amplifier as defined in claim 2 wherein said input limiting means are connected between said input terminals and exhibit a high impedance when said applied voltage is less than said first saturating level, and exhibit relatively low impedance when said applied voltag exceeds said first saturating level.

4. An unsaturable sense amplifier as defined in claim 3 wherein said input limiting means comprise a pair of Schottky diodes oppositely connected across said input terminals.

5. An unsaturable sense amplifier as defined in claim 1 wherein said output limiting means exhibit relatively high impedance when the output of said first amplifier means is less than said second saturating level, and exhibit relatively low impedance when said output of said first amplifier means exceeds said second saturating level.

6. An unsaturable sense amplifier as defined in claim 5 wherein said output limiting means comprise a pair of serially-connected, oppositely-sensed zener diodes.

7. An unsaturable sense amplifier as defined in claim 6 wherein said artifact squelch means include switch means coupled to the output of said second amplifier means and responsive to an applied control voltage, and comparator means for developing a control signal for rendering said switch means conductive when the output of said second amplifier means exceeds said squelch level.

8. An unsaturable sense amplifier as defined in claim 5 wherein said output limiting means comprise a pair of serially-connected, oppositely-sensed zener diodes connected between the input and output terminals of said second amplifier means.

9. An unsaturable sense amplifier for use in a pacer system analyzer to sense and amplify intracardiac signals induced in response to pacing pulses being applied to the heart of a patient, comprising:

first amplifier means comprising a differential amplifier having a pair of input terminals and responsive to the differential voltage between said input terminals for amplifying an applied voltage, said amplifier being subject to saturation by said applied voltage exceeding a first predetermined saturating level;

second amplifier means coupled to the output of said first amplifier means for amplifying said output of said first amplifier means, said second amplifier means being subject to saturation by said output exceeding a second predetermined saturating level;

input limiting means coupled to input terminals of said differential amplifier and exhibiting a relatively high impedance when said applied voltage is less than said first saturating level, and a relatively low impedance when said applied voltage exceeds said first saturating level, for limiting said applied voltage to less than said first predetermined saturating level;

output limiting means connected between the input and output of said second amplifier means, and exhibiting relatively high impedance when the output of said first amplifier means is less than said saturating level, and relatively low impedance when said output exceeds said second saturating level, for limiting said input of said second amplifier means to less than said second predetermined saturating level; and artifact squelch means coupled to said output of said second amplifier means for squelching said output when said output exceeds a predetermined squelch level.

10. An unsaturable sense amplifier as defined in claim 9 wherein said input limiting means comprise a pair of Schottky diodes oppositely connected across said input terminals.

* * * * *